United States Patent
Whitehurst et al.

(10) Patent No.: US 6,871,099 B1
(45) Date of Patent: Mar. 22, 2005

(54) FULLY IMPLANTABLE MICROSTIMULATOR FOR SPINAL CORD STIMULATION AS A THERAPY FOR CHRONIC PAIN

(75) Inventors: Todd K. Whitehurst, Sherman Oaks, CA (US); James P. McGivern, Stevenson Ranch, CA (US); Carla M. Mann, Los Angeles, CA (US); Janusz A. Kuzma, Englewood, CO (US)

(73) Assignee: Advanced Bionics Corporation, Valencia, CA (US)

( * ) Notice: Subject to any disclaimer, the term of this patent is extended or adjusted under 35 U.S.C. 154(b) by 314 days.

(21) Appl. No.: 09/929,597

(22) Filed: Aug. 13, 2001

Related U.S. Application Data
(60) Provisional application No. 60/226,333, filed on Aug. 18, 2000.

(51) Int. Cl.[7] .................................................. A61N 1/18
(52) U.S. Cl. ............................................. 607/46; 607/72
(58) Field of Search .............................. 607/46, 40, 41, 607/108, 58–62, 133, 116–118, 92, 148, 2, 70, 72, 74; 128/898, 899; 600/29, 30, 377; 604/20

(56) References Cited

U.S. PATENT DOCUMENTS

| | | | |
|---|---|---|---|
| 3,646,940 A | | 3/1972 | Timm et al. |
| 3,822,708 A | * | 7/1974 | Zilber .......................... 607/46 |
| 4,338,945 A | | 7/1982 | Kosugi et al. |
| 4,431,001 A | | 2/1984 | Hakansson et al. |
| 4,703,755 A | | 11/1987 | Tanagho et al. |
| 4,739,764 A | | 4/1988 | Lue et al. |
| 4,771,779 A | | 9/1988 | Tanagho et al. |
| 5,094,242 A | | 3/1992 | Gleason et al. |
| 5,193,539 A | | 3/1993 | Schulman et al. |
| 5,193,540 A | | 3/1993 | Schulman et al. |

(List continued on next page.)

FOREIGN PATENT DOCUMENTS

| | | |
|---|---|---|
| EP | 0245547 B1 | 8/1990 |
| WO | WO-98/37926 A1 | 9/1998 |
| WO | WO-98/43700 A1 | 10/1998 |
| WO | WO-98/43701 A1 | 10/1998 |
| WO | WO-01/52729 A2 | 7/2001 |

OTHER PUBLICATIONS

Cameron, et al., "Micromodular Implants to Provide Electrical Stimulation of Paralyzed Muscles and Limbs", IEEE Transactions on Biomedical Engineering, vol. 44, No. 9, (Sep. 1997), pp. 781–790.

Shealy, et al., "Electrical Inhibition of Pain by Stimulation of the Dorsal col.", Anesthesia and Analgesia, vol. 46, (1967), pp. 489–491.

(List continued on next page.)

*Primary Examiner*—Jeffrey R. Jastrzab
(74) *Attorney, Agent, or Firm*—Laura Haburay Bishop; Bryant R. Gold (57) ABSTRACT

An implantable stimulator(s), small enough to be located near or within an area of the spine responsible for sensations in a region experiencing chronic pain uses a power source/ storage device, such as a rechargeable battery. Periodic recharging of such a power source/storage device is accomplished, for example, by inductive coupling with an external appliance. The small stimulator provides a means of stimulating a nerve(s) or other tissue when desired, without the need for external appliances during the stimulation session. When necessary, external appliances are used for the transmission of data to and/or from the stimulator(s) and for the transmission of power, it necessary. In a preferred embodiment, the system is capable of open- and closed-loop operation. In closed-loop operation, at least one implant includes at least one sensor, and the sensed condition is used to adjust stimulation parameters.

18 Claims, 8 Drawing Sheets

U.S. PATENT DOCUMENTS

| | | | |
|---|---|---|---|
| 5,312,439 A | | 5/1994 | Loeb |
| 5,324,316 A | | 6/1994 | Schulman et al. |
| 5,330,515 A | * | 7/1994 | Rutecki et al. ............... 607/46 |
| 5,358,514 A | | 10/1994 | Schulman et al. |
| 5,405,367 A | | 4/1995 | Schulman et al. |
| 5,571,148 A | | 11/1996 | Loeb et al. |
| 5,702,428 A | | 12/1997 | Tippey et al. |
| 5,776,170 A | * | 7/1998 | MacDonald et al. .......... 607/46 |
| 5,824,021 A | * | 10/1998 | Rise ............................ 607/46 |
| 5,957,965 A | | 9/1999 | Moumane et al. |
| 5,984,854 A | | 11/1999 | Ishikawa et al. |
| 6,002,964 A | * | 12/1999 | Feler et al. .................... 607/46 |
| 6,018,682 A | * | 1/2000 | Rise ............................ 607/45 |
| 6,051,017 A | | 4/2000 | Loeb et al. |
| 6,058,331 A | * | 5/2000 | King ............................ 607/62 |
| 6,104,960 A | | 8/2000 | Duysens et al. |
| 6,161,044 A | * | 12/2000 | Silverstone .................. 607/45 |
| 6,185,452 B1 | | 2/2001 | Schulman et al. |
| 6,208,894 B1 | | 3/2001 | Schulman et al. |
| 6,208,902 B1 | * | 3/2001 | Boveja ........................ 607/46 |
| 6,240,316 B1 | | 5/2001 | Richmond et al. |
| 6,360,750 B1 | | 3/2002 | Gerber et al. |
| 6,464,687 B1 | | 10/2002 | Ishikawa et al. |
| 2001/0002441 A1 | | 5/2001 | Boveja |

OTHER PUBLICATIONS

Delaporte, et al., "Lumbrosacral Spinal Fibrosis (Spinal Arachnoiditis): Its Diagnosis and Treatment by Spinal Cord Stimulation", Spine, vol. 8, (1983), pp. 593–603.

North, et al., "Spinal Cord Stimulation for Chronic, Intractable Pain: Experience over Two Decades", Neurosurgery, vol. 32, No. 3, (1993) pp. 384–395.

Broseta, et al., "Chronic Epidural Dorsal Column Stimulation in the Treatment of Causalgia Pain", Appl Neurophysiol, vol. 45, (1982), pp. 190–194.

Krainich, et al., "Pain Reduction in Amputees by Long Term Spinal Cord Stimulation (5 year study)", J Neurosurg, vol. 52, (1980) pp. 346–350.

Jacobs, et al., "Epidural Spinal Cord Electrical Stimulation improves Microvascular Blood Flow in Severe Limb Ischemia", Annals of Surgery, vol. 207, No. 2, (1988), pp. 179–182.

Melzack, et al., "Pain Mechanisms: a New Theory", Science, vol. 150, (1965) pp. 971–979.

Loeb, Richmond, Mann, Faltys, Whitehurst, and McGivern inventors for AB–047U1, U.S. Appl. No. 09/642,979; filed Aug 18, 2000; entitled "Implantable Stimulator System and Method for Treatment of Incontinence and Pain".

* cited by examiner

FULLY IMPLANTABLE MICROSTIMULATOR FOR SPINAL CORD STIMULATION AS A THERAPY FOR CHRONIC PAIN

The present application claims the benefit of U.S. Provisional Patent Application Ser. No. 60/226,333, filed Aug. 18, 2000, which application is incorporated herein by reference in its entirety.

FIELD OF THE INVENTION

The present invention generally relates to implantable stimulator systems, and more particularly relates to an implantable stimulator system utilizing one or more implantable microstimulators for treating chronic pain.

BACKGROUND OF THE INVENTION

Chronic pain is usually a multidimensional phenomenon involving complex physiological and emotional interactions. For instance, one type of chronic pain, complex regional pain syndrome (CRPS)—which includes the disorder formerly referred to as reflex sympathetic dystrophy (RSD)—most often occurs after an injury, such as a bone fracture. The pain is considered "complex regional" since it is located in one region of the body (such as an arm or leg), yet can spread to additional areas. Since CRPS typically affects the sympathetic nervous system, which in turn affects all tissue levels (skin, bone, etc.), many symptoms may occur. Pain is the main symptom. Other symptoms vary, but can include loss of function, temperature changes, swelling, sensitivity to touch, and skin changes.

Another type of chronic pain, failed back surgery syndrome (FBSS), refers to patients who have undergone one or more surgical procedures and continue to experience pain. Included in this condition are recurring disc herniation, epidural scarring, and injured nerve roots.

Arachnoiditis, a disease that occurs when the membrane in direct contact with the spinal fluid becomes inflamed, causes chronic pain by pressing on the nerves. It is unclear what causes this condition.

Yet another cause of chronic pain is inflammation and degeneration of peripheral nerves, called neuropathy. This condition is a common complication of diabetes, affecting 60%–70% of diabetics. Pain in the lower limbs is a common symptom.

An estimated 10% of gynecological visits involve a complaint of chronic pelvic pain. In approximately one-third of patients with chronic pelvic pain, no identifiable cause is ever found, even with procedures as invasive as exploratory laparotomy. Such patients are treated symptomatically for their pain.

A multitude of other diseases and conditions cause chronic pain, including postherpetic neuralgia and fibromyalgia syndrome. Neurostimulation of spinal nerves, nerve roots, and the spinal cord has been demonstrated to provide symptomatic treatment in patients with intractable chronic pain.

Many other examples of chronic pain exist, as chronic pain may occur in any area of the body. For many sufferers, no cause is ever found. Thus, many types of chronic pain are treated symptomatically. For instance, many people suffer from chronic headaches/migraine and/or facial pain. As with other types of chronic pain, if the underlying cause is found, the cause may or may not be treatable. Alternatively, treatment may be only to relieve the pain.

All of the devices currently available for producing therapeutic stimulation have drawbacks. Many are large devices that must apply stimulation transcutaneously. For instance, transcutaneous electrical nerve stimulation (TENS) is used to modulate the stimulus transmissions by which pain is felt by applying low-voltage electrical stimulation to large peripheral nerve fibers via electrodes placed on the skin. TENS devices can produce significant discomfort and can only be used intermittently.

Other devices require that a needle electrode(s) be inserted through the skin during stimulation sessions. These devices may only be used acutely, and may cause significant discomfort.

Implantable, chronic stimulation devices are available, but these currently require a significant surgical procedure for implantation. Surgically implanted stimulators, such as spinal cord stimulators, have been described in the art. These spinal cord stimulators have different forms, but are usually comprised of an implantable control module to which is connected a series of leads that must be routed to nerve bundles in the spinal cord, to nerve roots and/or spinal nerves emanating from the spinal cord, or to peripheral nerves. The implantable devices are relatively large and expensive. In addition, they require significant surgical procedures for placement of electrodes, leads, and processing units. These devices may also require an external apparatus that needs to be strapped or otherwise affixed to the skin. Drawbacks, such as size (of internal and/or external components), discomfort, inconvenience, complex surgical procedures, and/or only acute or intermittent use has generally confined their use to patients with severe symptoms and the capacity to finance the surgery.

There are a number of theories regarding how stimulation therapies such as TENS machines and spinal cord stimulators may inhibit or relieve pain. The most common theory—gate theory or gate control theory—suggests that stimulation of fast conducting nerves that travel to the spinal cord produces signals that "beat" slower pain-carrying nerve signals and, therefore, override/prevent the message of pain from reaching the spinal cord. Thus, the stimulation closes the "gate" of entry to the spinal cord. It is believed that small diameter nerve fibers carry the relatively slower-traveling pain signals, while large diameter fibers carry signals of e.g., touch that travel more quickly to the brain.

Spinal cord stimulation (also called dorsal column stimulation) is best suited for back and lower extremity pain related to adhesive arachnoiditis, FBSS, causalgia, phantom limb and stump pain, and ischemic pain. Spinal cord stimulation is thought to relieve pain through the gate control theory described above. Thus, applying a direct physical or electrical stimulus to the larger diameter nerve fibers of the spinal cord should, in effect, block pain signals from traveling to the patient's brain. In 1967, Shealy and coworkers first utilized this concept, proposing to place stimulating electrodes over the dorsal columns of the spinal cord. (See Shealy C. N., Mortimer J. T., Reswick, J. B., "Electrical Inhibition of Pain by Stimulation of the Dorsal Column", in *Anesthesia and Analgesia,* 1967, volume 46, pages 489–491.) Since then, improvements in hardware and patient selection have improved results with this procedure.

The gate control theory has always been controversial, as there are certain conditions such as hyperalgesia, which it does not fully explain. The relief of pain by electrical stimulation of a peripheral nerve, or even of the spinal cord, may be due to a frequency-related conduction block which acts on primary afferent branch points where dorsal column fibers and dorsal horn collaterals diverge. Spinal cord stimulation patients tend to show a preference for a minimum pulse repetition rate of 25 Hz.

Stimulation may also involve direct inhibition of an abnormally firing or damaged nerve. A damaged nerve may be sensitive to slight mechanical stimuli (motion) and/or noradrenaline (a chemical utilized by the sympathetic nervous system), which in turn results in abnormal firing of the nerve's pain fibers. It is theorized that stimulation relieves this pain by directly inhibiting the electrical firing occurring at the damaged nerve ends.

Stimulation is also thought to control pain by triggering the release of endorphins. Endorphins are considered to be the body's own pain-killing chemicals. By binding to opioid receptors in the brain, endorphins have a potent analgesic effect.

Recently, an alternative to 1) TENS, 2) percutaneous stimulation, and 3) bulky implantable stimulation assemblies has been introduced. Small, implantable microstimulators have been introduced that can be injected into soft tissues through a cannula or needle. What is needed is a way to effectively use such small, fully implantable, chronic neurostimulators for the purpose of treating chronic pain.

BRIEF SUMMARY OF THE INVENTION

The invention disclosed and claimed herein addresses the above and other needs and provides means and systems for chronically stimulating a nerve root(s), spinal nerve(s), and/or spinal cord with a miniature implantable neurostimulator(s) that can be implanted via a minimal surgical procedure.

The nerve roots lie within the spinal column, and the spinal nerves exit the spinal column at the intervertebral foramen. To treat chronic pain, a miniature implantable electrical stimulator, such as a stimulator similar to a Bionic Neuron (also referred to as a BION™ microstimulator) may be implanted via a minimal surgical procedure (e.g., injection or small incision) in the spinal column, preferably adjacent to a dorsal root, for stimulation of a nerve root(s), and/or lateral to the intervertebral foramen for stimulation of a spinal nerve(s). Additionally or alternatively, a BION stimulator may be implanted in or on the spinal cord to stimulate, e.g., the dorsal column or the spinothalamic tract. A single microstimulator may be implanted, or two or more microstimulators may be implanted to achieve greater stimulation of one or more nerve roots, spinal nerves, and/or areas of the spinal cord. For instance, one or more microstimulator(s) may be implanted adjacent to the dorsal root of the third and/or fourth lumbar nerve (i.e., L3 and/or L4), and/or lateral to the intervertebral foramen of the third and/or fourth lumbar nerve.

Stimulation and control parameters of the implanted microstimulator are preferably adjusted to levels that are safe and efficacious with minimal patient discomfort. Different stimulation parameters generally have different effects on neural tissue, and parameters are thus chosen to target specific neural populations and to exclude others. For example, large diameter nerve fibers (e.g., A-α and/or A-β fibers) respond to relatively lower current density stimulation compared with small diameter nerve fibers (e.g., A-δ and/or C fibers).

According to one embodiment of the invention, chronic pain may be treated with stimulation to decrease excitement of targeted nerve roots, spinal nerves, and/or areas of the spinal cord; high-frequency electrical stimulation of such nerve fibers is likely to produce such inhibition. According to another embodiment of the invention, the stimulation can increase excitement of targeted nerve roots, spinal nerves, and/or areas of the spinal cord; low-frequency electrical stimulation of such nerve fibers is likely to produce such excitement.

The neurostimulator also includes a means of stimulating a nerve either intermittently or continuously. Specific stimulation parameters may provide therapeutic advantages for various forms of pain.

The microstimulator used with the present invention preferably possesses one or more of the following properties:

- at least two electrodes for applying stimulating current to surrounding tissue;
- electronic and/or mechanical components encapsulated in a hermetic package made from biocompatible material(s);
- an electrical coil or other means of receiving energy and/or information inside the package, which receives power and/or data by inductive or radio-frequency (RF) coupling to a transmitting coil placed outside the body, thus avoiding the need for electrical leads to connect devices to a central implanted or external controller;
- means for receiving and/or transmitting signals via telemetry;
- means for receiving and/or storing electrical power within the microstimulator; and
- a form factor making the microstimulator implantable via a minimal surgical procedure.

A microstimulator may operate independently, or in a coordinated manner with other implanted devices, or with external devices. In addition, a microstimulator may incorporate means for sensing pain, which it may then use to control stimulation parameters in a closed loop manner. According to one embodiment of the invention, the sensing and stimulating means are incorporated into a single microstimulator. According to another embodiment of the invention, a sensing means communicates sensed information to at least one microstimulator with stimulating means.

Thus, the present invention provides a therapy for chronic pain that utilizes one or more miniature neurostimulators and is minimally invasive. The simple implant procedure results in minimal surgical time and possible error, with associated advantages over known treatments in terms of reduced expense and opportunity for infection or other complications. Other advantages, inter alia, of the present invention include the system's monitoring and programming capabilities, the power source, storage, and transfer mechanisms, the activation of the device by the patient or clinician, the system's open and closed-loop capabilities and closed-loop capabilities coupled with sensing a need for and/or response to treatment, coordinated use of one or more stimulators, and the small size of the stimulator.

BRIEF DESCRIPTION OF THE DRAWINGS

The above and other aspects, features, and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

As indicated above, the present invention is directed to treating chronic pain using one or more small, implantable neurostimulators, referred to herein as "microstimulators". The microstimulators of the present invention are preferably similar to the type referred to as BION™ devices. The following documents describe various features and details associated with the manufacture, operation, and use of BION implantable microstimulators, and are all incorporated herein by reference:

| Application/Patent/ Publication No. | Filing/Publication Date | Title |
| --- | --- | --- |
| U.S. Pat. No. 5,193,539 | Issued Mar. 16, 1993 | Implantable Microstimulator |
| U.S. Pat. No. 5,193,540 | Issued Mar. 16, 1993 | Structure and Method of Manufacture of an Implantable Microstimulator |
| U.S. Pat. No. 5,312,439 | Issued May 17, 1994 | Implantable Device Having an Electrolytic Storage Electrode |
| U.S. Pat. No. 5,324,316 | Issued Jun. 28, 1994 | Implantable Microstimulator |
| U.S. Pat. No. 5,405,367 | Issued Apr. 11, 1995 | Structure and Method of Manufacture of an Implantable Microstimulator |
| PCT Publication WO 98/37926 | published Sep. 3, 1998 | Battery-Powered Patient Implantable Device |
| PCT Publication WO 98/43700 | published Oct. 8, 1998 | System of Implantable Devices For Monitoring and/or Affecting Body Parameters |
| PCT Publication WO 98/43701 | published Oct. 8, 1998 | System of Implantable Devices For Monitoring and/or Affecting Body Parameters |
| U.S. Pat. No. 6,051,017 (application Ser. No. 09/077,662) | Issued Apr. 18, 2000 | Improved Implantable Microstimulator and Systems Employing Same |
| | published September 1997 | Micromodular Implants to Provide Electrical Stimulation of Paralyzed Muscles and Limbs, by Cameron, et al., published in IEEE Transactions on Biomedical Engineering, Vol. 44, No. 9, pages 781–790. |

Figure 1A:
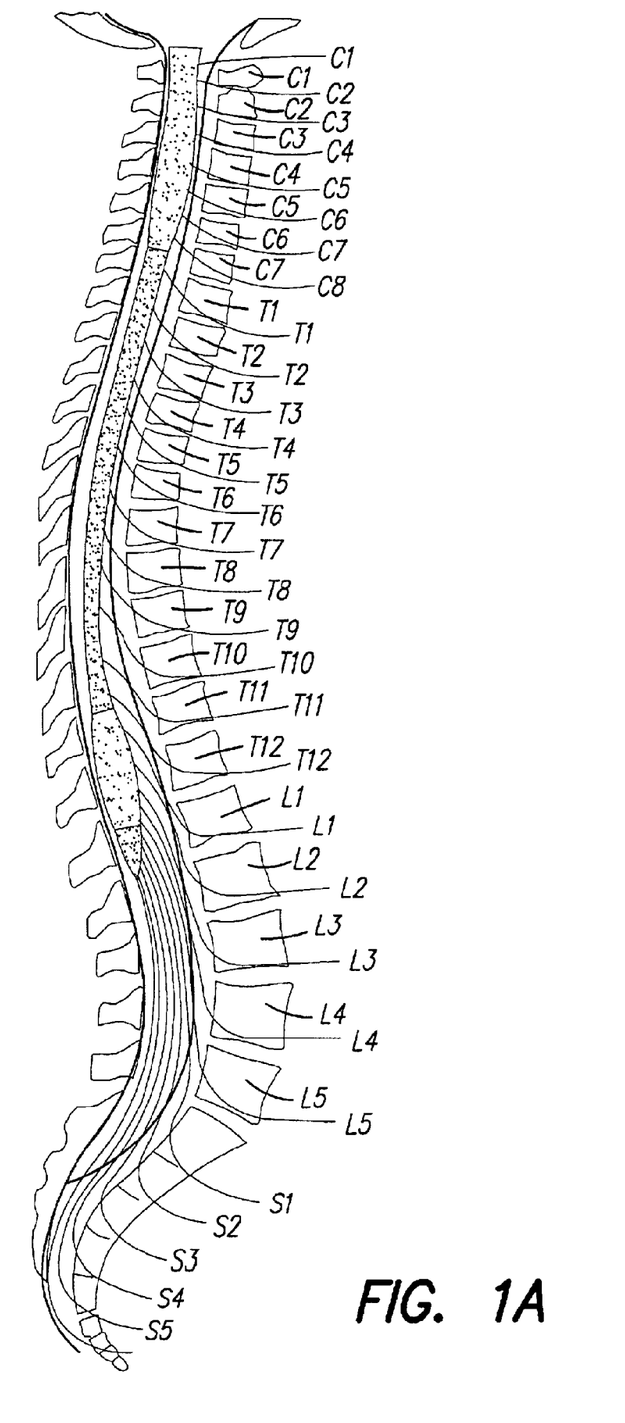
FIG. 1A illustrates the relation of spinal nerve roots to vertebrae.
Figure 1B:
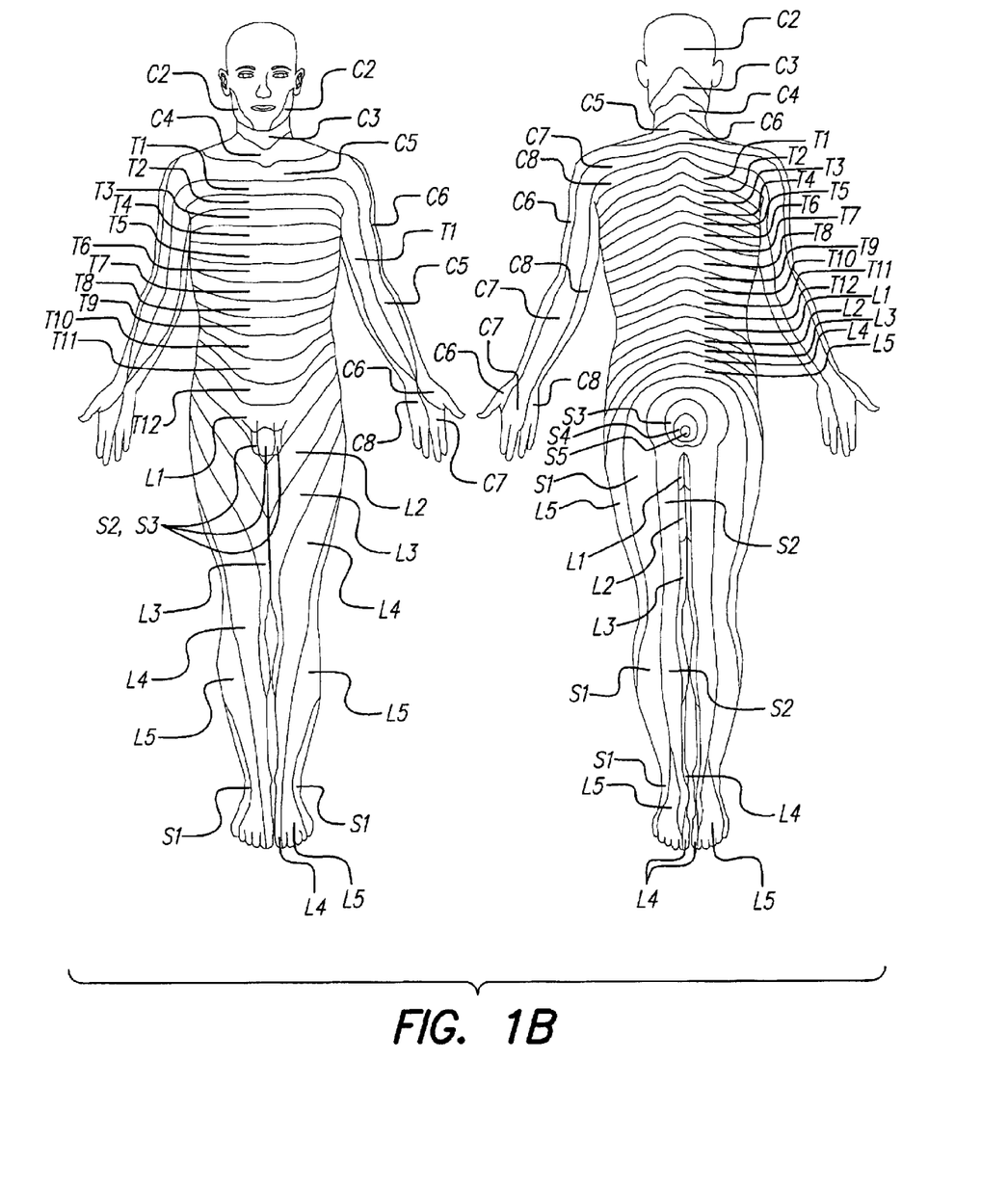
FIG. 1B illustrates the areas of skin innervated by the dorsal root axons at the various spinal levels.
Figure 2A:
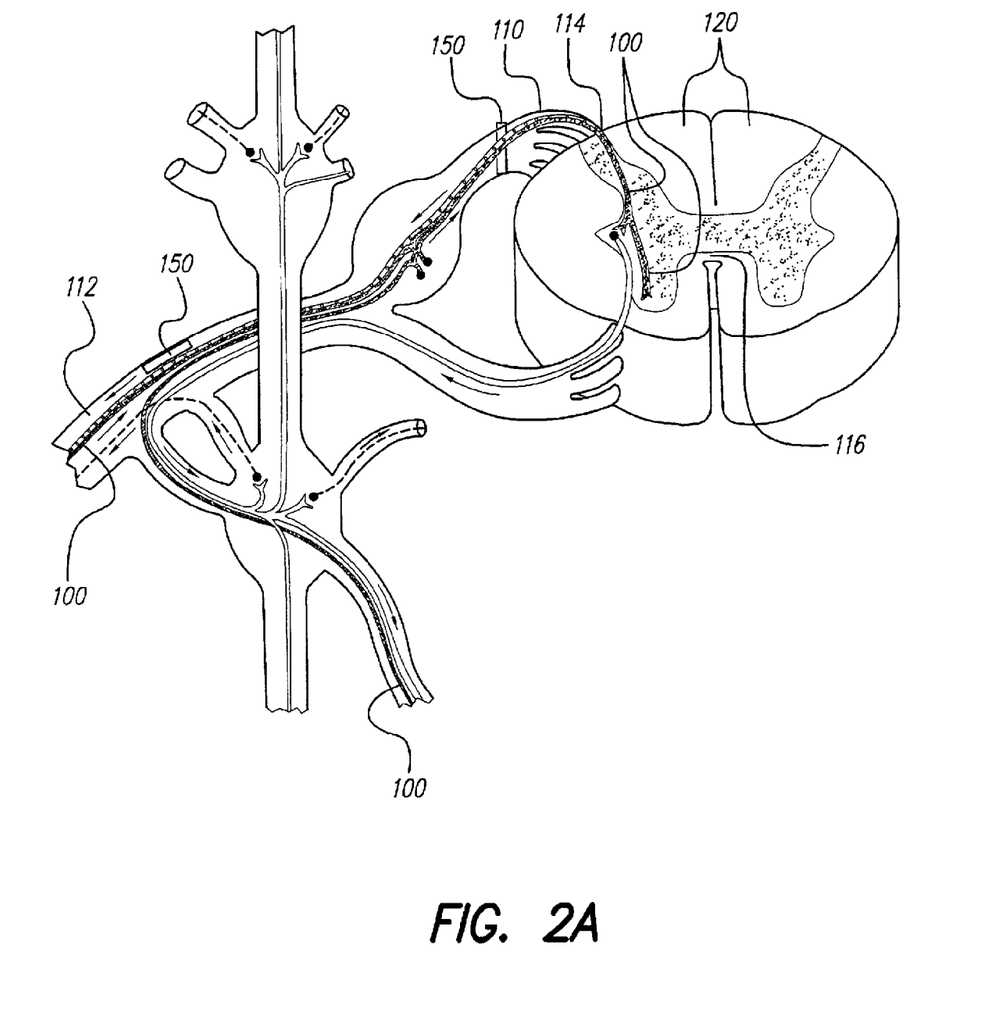
FIG. 2A depicts the nerve pathways in and near the thoracic part of the spinal cord.
Figure 2B:
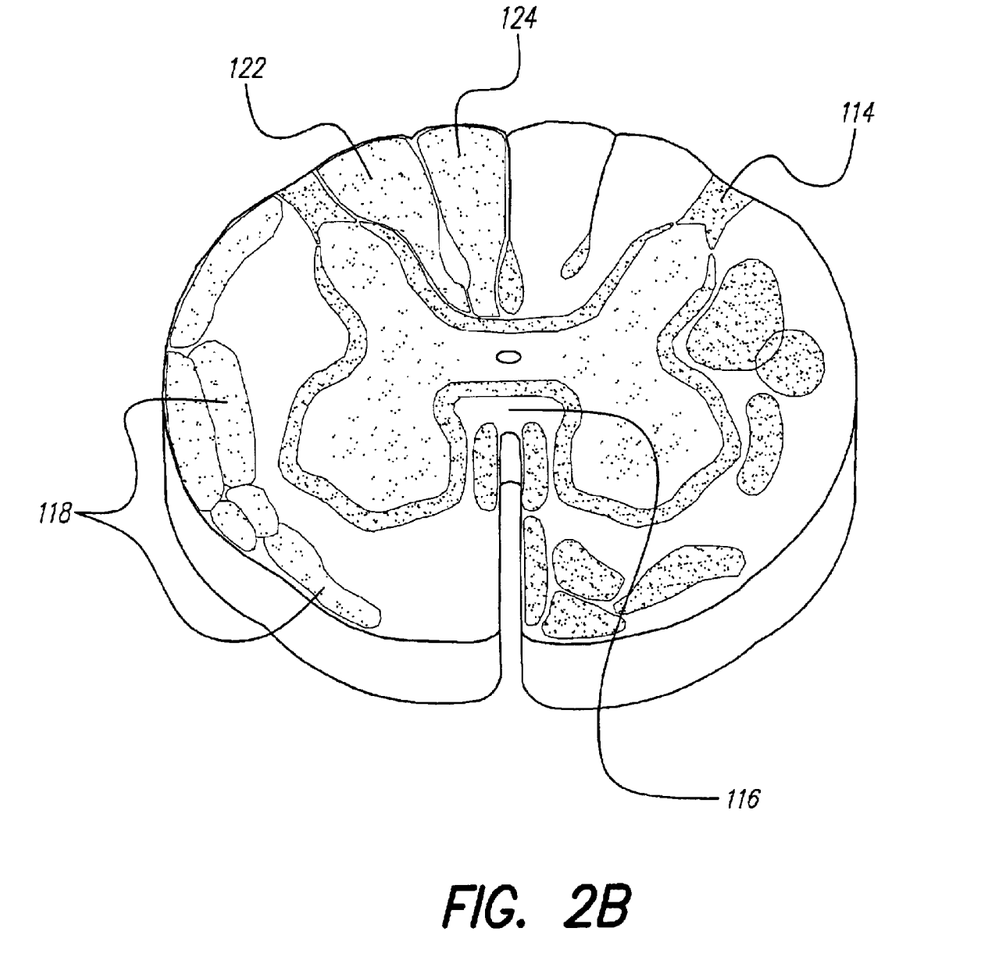
FIG. 2B illustrates the principal fiber tracts of the spinal cord.
Figure 3:
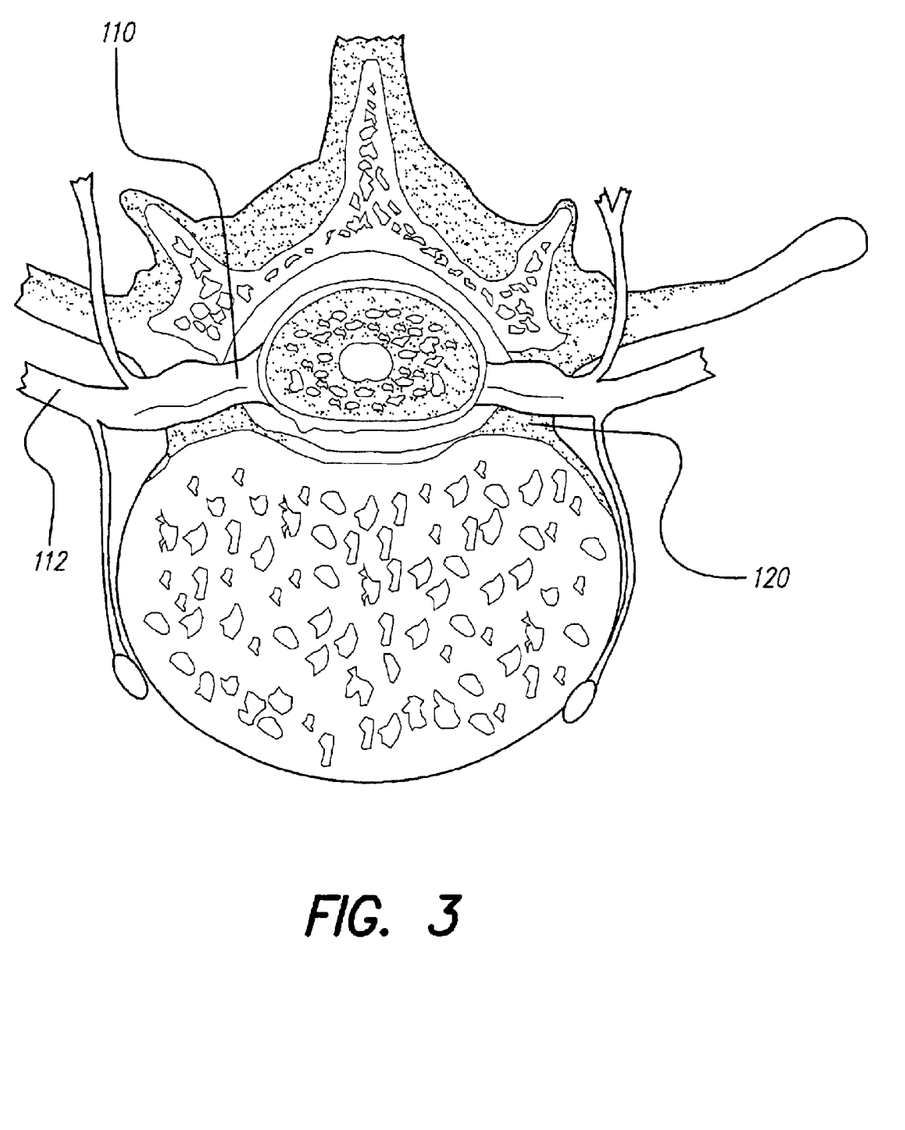
FIG. 3 depicts a section through a lumbar vertebra.

FIG. 1A illustrates the relation of spinal nerve roots to vertebrae, and FIG. 1B depicts the areas of skin innervated by the dorsal root axons at the various spinal levels, known as dermatomes. FIG. 2A illustrates the nerve pathways in and near the thoracic portion of the spinal cord, while FIG. 2B illustrates the principal fiber tracts of the spinal cord. FIG. 3 depicts a section through a lumbar vertebrae.

Among the most common complaints of chronic pain is pain in the limbs. As depicted in FIGS. 1A and 1B, the nerves in and near the spinal column from vertebra L1 down to the top portion of the sacrum (i.e., nerves L1, L2, L3, L4, L5, S1 and S2) have the greatest affect on sensations in the legs. Therefore, for example, in accordance with the teachings of the present invention, electrical stimulation at these same levels, L1–L5, S1, and S2, is provided to relieve leg pain.

Under normal conditions, pain signals are carried from the source of the pain through afferent nerve fibers which convey the impulses toward a nerve center (e.g., the brain or spinal cord). In the depictions of FIGS. 2A and 2B, the pain signals are carried toward the spinal cord via nerve fibers 100. The pain signals are then conducted up an ascending nerve pathway (via the spinothalamic tract 118 of the anterolateral system) to the brain, which processes the signals and induces the pain sensation. These pain signals travel through relatively small diameter nerve fibers (i.e., A-$\delta$ and C fibers) that enter the spinal cord at Lissauer's tract 114, decussate at the ventral commissure 116 over a distance of one to two spinal segments, then ascend to the brain within spinothalamic tract 118.

Figure 4:
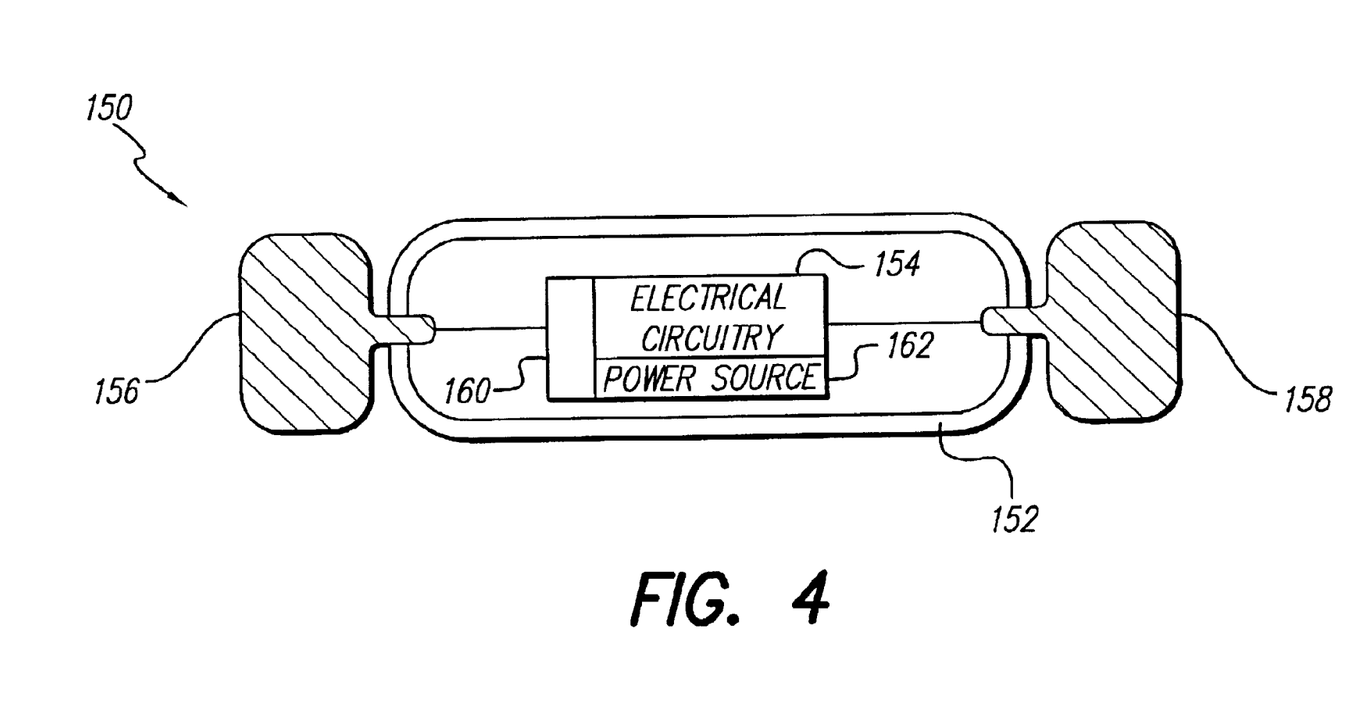
FIG. 4 illustrates an exemplary embodiment of a stimulation system of the present invention.

To treat chronic pain, a microminiature stimulator 150, such as a BION microstimulator, illustrated, e.g., in FIGS. 2A and 4, is preferably implanted e.g., adjacent to one or more dorsal (i.e., posterior) roots 110 and/or one or more spinal nerves 112. The nerve roots lie within the spinal column. The spinal nerves exit the spinal column at the intervertebral foramen 120 (FIG. 3). As seen in FIG. 2A, the microstimulator is placed on or near a spinal nerve 112, preferably lateral to intervertebral foramen 120, for stimulation of a spinal nerve(s).

Stimulating one or more dorsal nerve roots 110 and/or one or more spinal nerves 112, which would normally transmit pain sensations, should cause the pain to be eliminated, or moderated. Additionally or alternatively, stimulation of pain pathways in the spinal cord, such as along Lissauer's tract 114, the ventral commissure 116, and/or the spinothalamic tract 118 may be used to treat chronic pain.

Based on the gate control theory described earlier, stimulating fast-conducting, larger diameter nerve fibers will block, or gate, the slower pain signals from reaching the brain. The somatic sensory fibers responsible for touch, pressure, and position sense are carried through relatively large diameter nerve fibers (i.e., A-$\alpha$ and/or A-$\beta$ fibers) that enter the spinal cord and travel via a dorsal column 120, which is made up of the cuneate fasciculus 122 and the gracile fasciculus 124. As such, stimulation may additionally or alternatively be applied to these fibers as a treatment for chronic pain.

In accordance with the present invention, a single microstimulator 150 may be implanted, or two or more microstimulators may be implanted to achieve greater stimulation of the targeted tissue, or for a longer period of time. As shown in FIG. 4, microstimulator device 150 includes a narrow, elongated capsule 152 containing electronic circuitry 154 connected to electrodes 156 and 158, which pass through the walls of the capsule at either end. As detailed in the referenced patent publications, electrodes 156 and 158 comprise a stimulating electrode (to be placed close to the nerve) and an indifferent electrode (for completing the circuit). Other preferred configurations of microstimulator device 150 are possible, as is evident from the above-referenced patent publications.

Advantageously, a preferred implantable microstimulator 150 is sufficiently small to permit its placement near the structures to be stimulated. (As used herein, "adjacent" and "near" mean as close as reasonably possible to targeted tissue, including touching or even being positioned within the tissue, but in general, may be as far as about 150 mm from the target tissue.) Capsule 152 preferably has a diameter no greater than about 4–5 mm, more preferably only about 3 mm, and most preferably less than about 3 mm. Capsule length is preferably no greater than about 25–35 mm, more preferably only about 20–25 mm, and most preferably less than about 20 mm. The shape of the microstimulator is preferably determined by the structure of the desired target, the surrounding area, and the method of insertion. A thin, elongated cylinder with electrodes at the ends, as shown in FIG. 4, is currently preferred, but other shapes, such as spheres, disks, or helical structures, are possible.

Microstimulator 150 is preferably implanted with a surgical insertion tool specially designed for the purpose, or is injected (e.g., via a hypodermic needle). Alternatively, device 150 may be implanted via conventional surgical methods, or may be inserted using other endoscopic or laparoscopic techniques. A more complicated surgical procedure may be required for purposes of fixing the microstimulator in place.

The external surfaces of stimulator 150 are advantageously composed of biocompatible materials. Capsule 152 is preferably made of glass, ceramic, or other material that provides a hermetic package that will exclude water vapor but permit passage of electromagnetic fields used to transmit data and/or power. Electrodes 156 and 158 are preferably made of a noble or refractory metal or compound, such as platinum, iridium, tantalum, titanium, titanium nitride, niobium, or alloys of any of these, in order to avoid corrosion or electrolysis which could damage the surrounding tissues and the device.

In one preferred embodiment of the instant invention, microstimulator 150 comprises two, leadless electrodes. However, either or both electrodes 156 and 158 may be located at the ends of short, flexible leads as described in U.S. patent application Ser. No. 09/624,130, filed Jul. 24, 2000 (which claims priority to U.S. Provisional Patent Application No. 60/156,980, filed Oct. 1, 1999), which is incorporated herein by reference in its entirety. Other configurations may also permit electrical stimulation to be directed more locally to specific tissue a short distance from the surgical fixation of the bulk of the implantable stimulator 150, while allowing elements of stimulator 150 to be located in a more surgically convenient site. Such configurations minimize the distance traversed and the surgical planes crossed by the device and any lead(s), which herein defines any means to locally direct the electrical stimulation. In a preferred embodiment, the leads (i.e., directing means) are no longer than about 150 mm.

Microstimulator 150 preferably contains electronic circuitry 154 for receiving data and/or power from outside the body by inductive, radio-frequency (RF), or other electromagnetic coupling. In a preferred embodiment, electronic circuitry 154 includes an inductive coil for receiving and transmitting RF data and/or power, an integrated circuit (IC) chip for decoding and storing stimulation parameters and generating stimulation pulses (either intermittent or continuous), and additional discrete electronic components required to complete the electronic circuit functions, e.g. capacitor(s), resistor(s), coil(s), and the like.

In some preferred embodiments, microstimulator 150 advantageously includes a programmable memory 160 for storing a set(s) of stimulation and control parameters, if required. This feature allows stimulation and control parameters to be adjusted to settings that are safe and efficacious with minimal discomfort for each individual. Specific parameters may provide therapeutic advantages for various forms and severity of pain. For instance, some patients may respond favorably to intermittent stimulation, while others may require continuous stimulation to alleviate their pain.

In addition, stimulation parameters are typically chosen to target specific neural populations and to exclude others. For example, relatively low frequency neurostimulation (i.e., less than about 100–150 Hz) may have an excitatory effect on surrounding neural tissue, whereas relatively high frequency neurostimulation (i.e., greater than about 100–150 Hz) may have an inhibitory effect. In addition, large diameter fibers (e.g., A-$\alpha$ and/or A-$\beta$ fibers) respond to relatively lower current density stimulation compared with small diameter fibers (e.g., A-$\delta$ and/or C fibers).

The preferred implantable stimulator 150 also includes a power source and/or power storage device 162. Possible power options, described in more detail below, include but are not limited to an external power source coupled to stimulator 150 via an RF link, a self-contained power source utilizing any means of generation or storage of energy (e.g., a primary battery, a rechargeable battery such as a lithium ion battery, an electrolytic capacitor, or a super- or ultra-capacitor), and if the self-contained power source is replenishable or rechargeable, means of replenishing or recharging the power source (e.g., an RF link, an optical link, a thermal link, or other energy-coupling link).

According to one embodiment of the invention, a microstimulator operates independently. According to another embodiment of the invention, a microstimulator operates in a coordinated manner with other microstimulator(s), other implanted device(s), or other device(s) external to the patient's body. For instance, a microstimulator may control or operate under the control of another implanted microstimulator(s), other implanted device(s), or other device(s) external to the patient's body. A microstimulator may communicate with other implanted microstimulators, other implanted devices, and/or devices external to a patient's body via, e.g., an RF link, an ultrasonic link, a thermal link, or an optical link. Specifically, a microstimulator may communicate with an external remote control (e.g., patient and/or physician programmer) that is capable of sending commands and/or data to a microstimulator and that is preferably capable of receiving commands and/or data from a microstimulator.

In order to help determine the strength of electrical stimulation required to produce the desired therapeutic effect, in one preferred embodiment, a patient's response to and/or need for treatment is sensed, such as sensing changes in levels of pain medication. Thus, when implantable stimulator 150 is implanted, for example, near a spinal nerve(s) 112, the signals from a sensor built into microstimulator 150 are used to adjust stimulation parameters. Alternatively, a "microstimulator" dedicated to sensory processes may communicate with a microstimulator that provides the stimulation pulses. As described below, the implant circuitry 154 amplifies and transmits these sensed signals, which may be analog or digital. Other methods of determining the required stimulation include a sensor on the hypogastric plexus for sensing increased sympathetic discharge and other markers of the potential for pain, as well as other methods mentioned herein, and yet others that will be evident to those of skill in the art upon review of the present disclosure. The sensed information is preferably used to control the electrical and/or control parameters in a closed-loop manner.

Figure 5:
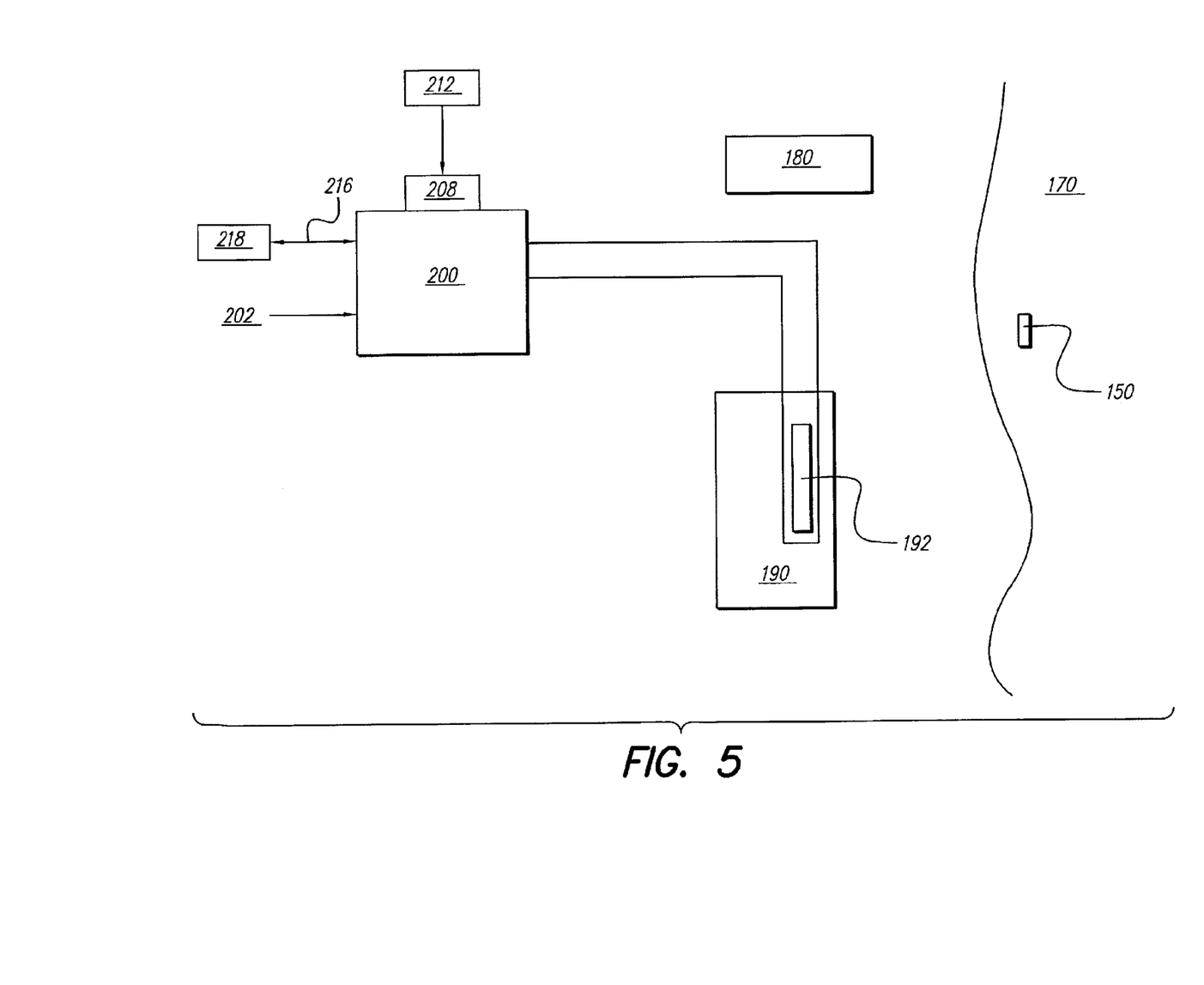
FIG. 5 illustrates preferred external components of the invention.

In operation, as illustrated in FIG. 5, the patient 170 turns the implantable stimulator 150 on and off by use of controller 180, which is preferably handheld. Implantable stimulator 150 is operated by controller 180 by any of various means, including sensing the proximity of a permanent magnet located in controller 180, or sensing RF transmissions from controller 180.

External components of one preferred embodiment for programming and/or providing power to the implantable stimulator 150 are also illustrated in FIG. 5. When it is required to communicate with the implanted stimulator 150, the patient 170 is positioned on or near external appliance 190, which appliance contains one or more inductive coils 192 or other means of communication (e.g., RF transmitter and receiver). External appliance 190 is connected to or is a part of external electronic circuitry appliance 200 which receives power 202 from a conventional power source. External appliance 200 contains manual input means 208, e.g., a keypad, whereby the patient 170 or a caregiver 212 can request changes in the stimulation parameters produced during the normal operation of the implantable stimulator 150. In this preferred embodiment, the manual input means 208 includes various electro-mechanical switches and/or visual display devices that provide the patient and/or caregiver with information about the status and prior programming of the implantable stimulator 150.

Alternatively or additionally, the external electronic appliance 200 is provided with an electronic interface means 216 for interacting with other computing means 218, such as by a serial interface cable or infrared link to a personal computer or to a telephone modem. Such interface means 216 thus permits a clinician to monitor the status of the implant and prescribe new stimulation parameters from a remote location.

The external appliance(s) may advantageously be embedded in a cushion, mattress cover, or garment. Other possibilities exist, including a belt or other structure that may be affixed to the patient's body or clothing.

Thus, it is seen that in accordance with the present invention, one or more external appliances are preferably provided to interact with microstimulator 150 to accomplish one or more of the following functions:

Function 1: if necessary, transmit electrical power from the external electronic appliance 200 via appliance 190 to the implantable stimulator 150 in order to power the device and/or recharge the power source/storage device 162. External electronic appliance 200 may include an automatic algorithm that adjusts stimulation parameters automatically whenever the implantable stimulator(s) 150 is/are recharged.

Function 2: Transmit data from the external appliance 200 via the external appliance 190 to the implantable stimulator 150 in order to change the operational parameters (e.g., electrical stimulation parameters) used by stimulator 150.

Function 3: Transmit sensed data indicating a need for treatment or in response to stimulation (e.g., impedance, muscle activity (e.g., EMG), nerve activity (e.g., ENG), electrical activity of the brain (e.g., EEG), or other activity) from implantable stimulator 150 to external appliance 200 via external appliance 190.

Function 4: Transmit data indicating state of the implantable stimulator 150 (e.g., battery level, stimulation settings, etc.) to external appliance 200 via external appliance 190.

By way of example, a treatment modality for chronic lower extremity and low back pain is carried out according to the following sequence of procedures:

1. A stimulator 150 is implanted so that its electrodes 156 and 158 are lateral to the intervertebral foramen 120 of vertebra L3 (for stimulation of spinal nerve 112).
2. Using Function 2 described above (i.e., transmitting data) of external electronic appliance 200 and external appliance 190, implantable stimulator 150 is commanded to produce a series of electrical stimulation pulses with gradually increasing amplitude.
3. Set stimulator on/off period to an appropriate setting, e.g., five seconds on then one second off.
4. After each stimulation pulse, series of pulses, or some predefined interval, any change in impedance is sensed, preferably by one or more electrodes 156 and 158 of implantable stimulator 150. These responses are converted to data and telemetered out to external electronic appliance 200 via Function 3.
5. From the response data received at external appliance 200 from the implantable stimulator 150, or from other assessment, the stimulus threshold for obtaining a reflex response is determined and is used by a clinician acting directly 212 or by other computing means 218 to transmit the desired stimulation parameters to the implantable stimulator 150 in accordance with Function 2.
6. When patient 170 desires to invoke an electrical stimulation to alleviate symptoms (e.g., pain, loss of function, etc.), patient 170 employs handheld controller 180 to set the implantable stimulator 150 in a state where it delivers the prescribed stimulation pattern.
7. Patient 170 employs controller 180 to turn off stimulator 150, if desired.
8. Periodically, the patient or caregiver recharges the power source/storage device 162 of implantable stimulator 150 in accordance with Function 1 described above (i.e., transmit electrical power).

For the treatment of any of the various types and degrees of chronic pain, it may be desirable to modify or adjust the algorithmic functions performed by the implanted and/or external components, as well as the surgical approaches, in ways that would be obvious to skilled practitioners of these arts. For example, it may be desirable to employ more than one implantable stimulator 150, each of which could be separately controlled by means of a digital address. Multiple channels and/or multiple patterns of stimulation might thereby be programmed by the clinician and controlled by the patient in order to deal with bilateral, complex, or multidimensional pain such as may occur as a result of spinal cord injury and failed back surgery syndrome (FBSS), for example.

In one preferred embodiment, microstimulator 150, or a group of two or more microstimulators, is controlled via closed-loop operation. A need for and/or response to stimulation is sensed via microstimulator 150, or by an additional microstimulator (which may or may not be dedicated to the sensing function), or by another implanted or external device. If necessary, the sensed information is transmitted to microstimulator 150. Preferably, the stimulation parameters used by microstimulator 150 are automatically adjusted based on the sensed information. Thus, the stimulation parameters are adjusted in a closed-loop manner to provide stimulation tailored to the response to stimulation.

For instance, in one embodiment of the present invention, a first and second "stimulator" are provided. The second "stimulator" periodically (e.g. once per minute) records a level of e.g., neural activity, which it transmits to the first stimulator. The first stimulator uses the sensed information to adjust stimulation parameters according to an algorithm programmed, e.g., by a physician. For example, amplitude of stimulation may be increased in response to increased neural activity. More preferably, one "microstimulator" performs both the sensing and current generating functions.

Figure 6:
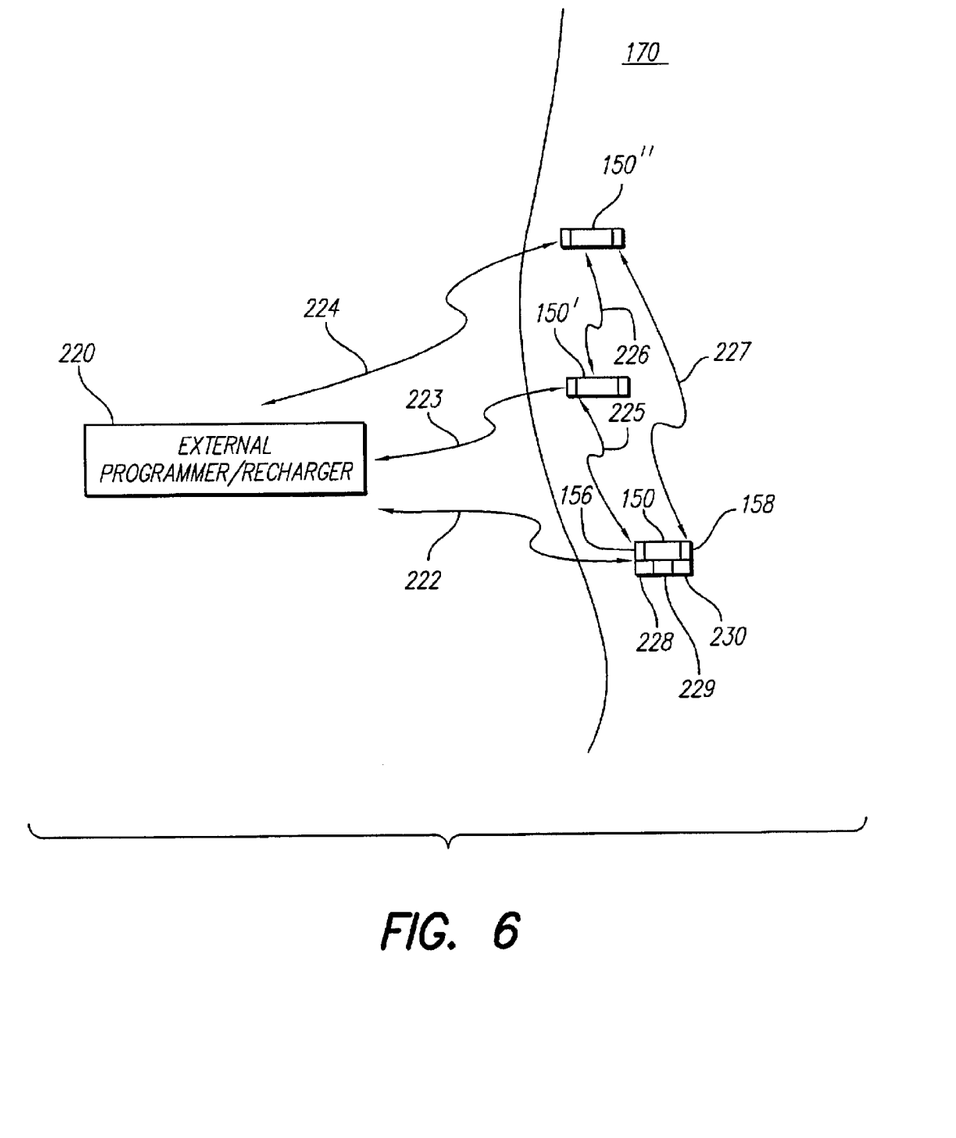
FIG. 6 depicts a system of implantable devices that communicate with each other and/or with external control/programming devices.

For example, as seen in FIG. 6, a first microstimulator 150, implanted in or adjacent the spine of patient 170, provides electrical stimulation via electrodes 156 and 158 to a first location; a second microstimulator 150' provides electrical stimulation to a second spinal location; and a third microstimulator 150" provides electrical stimulation to a third spinal location. As mentioned earlier, the implanted devices may operate independently or may operate in a coordinated manner with other similar implanted devices, other implanted devices, or other devices external to the patient's body, as shown by the control lines 222, 223 and 224 in FIG. 6. That is, in accordance with one embodiment of the invention, the external controller 220 controls the operation of each of the implanted microstimulators 150, 150' and 150'. According to another embodiment of the invention, an implanted device, e.g. microstimulator 150, may control or operate under the control of another implanted device(s), e.g. microstimulator 150' and/or microstimulator 150'. That is, a device made in accordance with the invention may communicate with other implanted stimulators, other implanted devices, and/or devices external to a patient's body, e.g., via an RF link, an ultrasonic link, a thermal link, or an optical link. Specifically, as illustrated in FIG. 6, microstimulator 150, 150', and/or 150", made in accordance with the invention, may communicate with an external remote control (e.g., patient and/or physician programmer 220) that is capable of sending commands and/or data to implanted devices and that is capable of receiving commands and/or data from implanted devices.

Microstimulators made in accordance with the invention further incorporate, in one embodiment, first sensing means 228 for sensing therapeutic effects, clinical variables, or other indicators of the state of the patient, such as impedance, EMG, ENG, and/or EEG. The stimulators additionally or alternatively incorporate second means 229 for sensing levels and/or changes in pain medication and/or sympathetic discharge and/or other markers of the potential for pain. The stimulators additionally or alternatively incorporate third means 230 for sensing electrical current levels and waveforms supplied by another source of electrical energy. Sensed information may then be used to control the parameters of the stimulator(s) in a closed loop manner, as shown by control lines 225, 226, and 227. Thus, the sensing means may be incorporated into a device that also includes electrical stimulation means, or the sensing means (that may or may not have stimulating means), may communicate the sensed information to another device(s) with stimulating means.

While a microstimulator may also incorporate means of sensing pain, it may alternatively or additionally be desirable to use a separate or specialized implantable device to sense and telemeter physiological conditions/responses in order to adjust stimulation parameters. This information may then be transmitted to an external device, such as external appliance 220, or may be transmitted directly to implanted stimulator(s) 150. However, in some cases, it may not be necessary or desired to include a sensing function or device, in which case stimulation parameters are determined and refined, for instance, by patient feedback.

As described earlier, microstimulator 150 includes means to stimulate intermittently or continuously. Specific stimulation parameters provide therapeutic advantages for various forms of pain.

According to one therapeutic alternative, pain is alleviated with decreased excitement of targeted neural tissue, e.g., at decussation of the spinothalamic tract, at the ventral commissure 116. High-frequency electrical stimulation (e.g., greater than about 100–150 Hz) is likely to produce such inhibition. Depending on the specific condition of a patient, this therapy is most likely to provide relief to patients with chronic peripheral pain, such as peripheral neuropathy and complex regional pain syndrome (CRPS), among other problems. Alternatively or additionally, the patient may be treated with decreased excitement of other areas of the spinal cord through which pain signals travel, such as Lissauer's tract, or at other locations along the spinothalamic tract 118.

According to another therapeutic alternative, pain is alleviated with increased excitement of one or more of dorsal column(s) 120 (cuneate fasciculus 122 and/or gracile fasciculus 124), dorsal root(s) 110, and/or spinal nerve(s) 112, at e.g., TB–S5, and/or more preferably T10–S1. Low-frequency electrical stimulation (e.g., less than about 100–150 Hz) is likely to produce such excitement. This therapy is most likely to provide relief to patients with CRPS and FBSS, among other problems.

As mentioned earlier, large diameter fibers (e.g., A-α and/or A-β fibers) respond to relatively lower current density stimulation vis-à-vis small diameter fibers (e.g., A-δ and/or C fibers). These A-δ and C fibers are generally responsible for carrying pain and temperature signals, while the A-α and A-β fibers generally carry pressure, light touch, and proprioceptive information. Therefore, pain may be masked, decreased or removed by activating the larger A-α and/or A-β fibers, so the signals from the A-δ and/or C fibers are "masked", or "gated." For example, microstimulator(s) 150 may be implanted on or adjacent a dorsal column 120 or a dorsal root 110 of one or more of L2, L3, L4, and L5 to treat pain at the front of a patient's leg (see FIG. 1B). The microstimulator(s) are preferably programmed to provide relatively low-current stimulation pulses (e.g., at less than about 1–10 mA, depending on proximity of the stimulator to the target neural tissue), which is likely to cause the sensation of pressure, light touch, proprioceptive, and other non-nociceptive sensations. These sensations may be sufficient to mask or block the pain signals.

If, instead or additionally, the pain is located at the back of a patient's leg and/or in the foot, stimulation applied to one or more nerve fibers of L1–L5, S1, and S2 may provide relief. As used herein, nerve fibers include spinal nerve(s), spinal nerve root(s), and areas in and around the spinal cord, such as Lissauer's tract, the ventral commissure, the spinothalamic tract, the dorsal column, among other things. Chronic pain in the arms may best be relieved with stimulation of one or more nerve fibers of C5, C6, C7, C8, and T1. Chronic cervical pain may best be relieved with stimulation of one or more nerve fibers of C2–C5, while chronic pain in the lower back may best be treated with stimulation of one or more nerve fibers of L1–L5, and S1. Pain elsewhere in the back may best be treated with stimulation of one or more nerve fibers of T1–T12. Pain in the head/neck region, such as headache, migraine, facial pain, and/or occipital neuralgia may be best treated with stimulation of one or more nerve fibers of C1–C8.

As described earlier, chronic pain is often reported in the pelvic region. For pain in this area, preferred locations for a stimulator(s) include one or more of the nerve fibers of T10–T12, L1, and L2 (mainly for pain in the front half of the pelvis), and/or L1–L5 and S1 —S5 (for pain in the back half of the pelvis).

In yet another alternative, sensing means described earlier may be used to orchestrate first the activation of microstimulator(s) targeting one or more nerves to control pain in one area, and then, when appropriate, the microstimulator(s) targeting nerves that control pain in another area and/or by a different means. Alternatively, this orchestration may be programmed, and not based on a sensed condition.

While the invention herein disclosed has been described by means of specific embodiments and applications thereof, numerous modifications and variations could be made thereto by those skilled in the art without departing from the scope of the invention set forth in the claims.

What is claimed is:

1. A method for treating a patient with chronic pain, comprising:
   providing at least one stimulator having at least two electrodes;
   implanting the at least one stimulator in at least one anterolateral area of the spine responsible for sensations in a region experiencing chronic pain;
   providing operating power to the at east one stimulator;
   providing stimulation parameters to the at least one stimulator;
   generating stimulation pulses in accordance with the stimulation parameters; and
   delivering the stimulation pulses to nerves and tissue of the anterolateral spinal cord via the at least two electrodes;
   wherein the at least one area of the spine comprises the ventral commissure; and
   wherein the stimulator has a size and shape suitable for placement in the at least one anterolateral area of the spine.

2. The method of claim 1 wherein the stimulation pulses are delivered at greater than about 100 Hz.

3. The method of claim 1 wherein the chronic pain is located in one or both arms, and the at least one stimulator is implanted adjacent to at least one nerve fibers of C5, C6, C7, C8, and T1.

4. The method of claim 1 wherein the chronic pain is located in one or both legs, and the at least one stimulator is implanted adjacent to at least one nerve fiber of L1–L5, S1, and S2.

5. The method of claim 1 wherein the chronic pain is located in the pelvic region, and the at least one stimulator is implanted adjacent to at least one nerve fibers of T10, T11, T12, L1 L5, and S1–S5.

6. The method of claim 1 wherein the chronic pain is located in the back, and the at least one stimulator is implanted adjacent to at least one nerve fibers of T1–T12, L1–L5, and S1.

7. The method of claim 1 wherein the chronic pain is located in the cervical region, and the at least one stimulator is implanted adjacent to at least one nerve fibers of C2, C3, C4, and C5.

8. The method of claim 1 wherein the chronic pain is located in the head/neck region, and the at least one stimulator is implanted adjacent to at least one nerve fiber of C1–C8.

9. The method of claim 1 further comprising:
   providing at least one sensor;
   using the at least one sensor to sense at least one physical condition; and
   determining the stimulation parameters based upon the at least one sensed condition.

10. The method of claim 1 wherein providing stimulation parameters comprises receiving the stimulation parameters from at least one external appliance.

11. The method of claim 1 wherein providing operating power comprises receiving the operating power from at least one external appliance.

12. The method of claim 1 further comprising providing and implanting more than one stimulator.

13. A method for treating a patient with chronic pain, comprising the steps of:
   providing at least one means for stimulating tissue;
   implanting the at least one stimulating means in at least one anterolateral area of the spine responsible for sensations in a region experiencing chronic pain;
   providing operating power to the at least one stimulating means;
   providing stimulation parameters to the at least one stimulating means;
   generating stimulation pulses in accordance with the stimulation parameters; and
   delivering the stimulation pulses to nerves and tissue of the anterolateral spinal cord via the at least one stimulating means;
   wherein the at least one area of the spine comprises the ventral commissure; and
   wherein the stimulating means has a size and shape suitable for placement in the at least one anterolateral area of the spine and has leads up to 150 mm long.

14. The method of claim 13 wherein the body of the stimulator is no more than 150 mm from the nerve to be stimulated.

15. The method of claim 13 wherein the stimulation parameters are determined using at least one external appliance.

16. The method of claim 13 wherein providing operating power to the at least one stimulator comprises receiving power from at least one external appliance.

17. The method of claim 16 wherein providing power to the at least one stimulator further comprises storing the power received from the at least one external appliance.

18. The method of claim 13 further comprising providing and implanting more than one stimulator.

* * * * *